United States Patent [19]
Mettes

[11] Patent Number: 5,199,295
[45] Date of Patent: Apr. 6, 1993

[54] FEEDBACK CONTROLLED GAS MIXTURE GENERATOR ESPECIALLY FOR AN HYGROMETER REACTION CHECK

[75] Inventor: Jacob Mettes, Doylestown, Pa.

[73] Assignee: Meeco, Inc., Warrington, Pa.

[21] Appl. No.: 644,081

[22] Filed: Jan. 22, 1991

[51] Int. Cl.$^5$ .............. G01C 17/38; B01F 3/02
[52] U.S. Cl. .................. 73/1 G; 73/29.01; 236/44 A
[58] Field of Search .......... 73/1 G, 29.01, 29.02, 73/31.02, 23.21; 236/44 R, 44 A; 422/83

[56] References Cited

U.S. PATENT DOCUMENTS 3,614,855 10/1971 Van Luik, Jr. .......... 73/1 G
4,356,834 11/1982 LeMay ................ 137/89
4,625,543 12/1986 Ertl et al. ............. 73/1 G

FOREIGN PATENT DOCUMENTS 3632698 3/1988 Fed. Rep. of Germany ....... 73/1 G

OTHER PUBLICATIONS

Diffusion Cell, Analytical Chemistry, vol. 46 Aug. 1975 pp. 1705-1707.
K. Sugiyama & T. Ohmi, "Ultraclean Gas Delivery Systems—Part I", in *Microcontamination* at 49-54 (Nov. 1988).
T. Kimura, J. Mettes & M. Schack, "Sub-ppb Analysis of Nitrogen Gas by APIMS":, presented at Technical Symposium of SEMICON EAST 89 in Boston, Mass. (Sep. 1989).

*Primary Examiner*—William E. Wayner
*Attorney, Agent, or Firm*—Ratner & Prestia

[57] ABSTRACT

A small moisture addition apparatus which regularly, through use of a counterflow, adds a controlled amount of moisture to a sample gas analyzed by an hygrometer to reduce the response time of the hygrometer and to provide automatic verification that the hygrometer is functioning. A method of using that apparatus is also disclosed. The apparatus and method of the present invention can be applied to gas components other than moisture and to the detectors of such components.

26 Claims, 8 Drawing Sheets

FEEDBACK CONTROLLED GAS MIXTURE GENERATOR ESPECIALLY FOR AN HYGROMETER REACTION CHECK

FIELD OF THE INVENTION

This invention relates to a method and an apparatus for generating low moisture concentrations. The method and apparatus are especially useful for checking, on line, the functionality of an hygrometer and for assuring a rapid response by that instrument to an increase in the moisture concentration of the sample gas monitored by the hygrometer. More specifically, minute amounts of moisture, regulated by a counterflow, are added to the sample gas before it reaches the hygrometer and the hygrometer provides a feedback signal to control the addition in a precise manner.

BACKGROUND OF THE INVENTION

In many industrial processes, the presence and amount of even minute moisture concentrations in flowing gas streams must be detected and measured with a high degree of speed and accuracy. The process of manufacturing semiconductors uses flowing gas streams, for example, and any moisture present in those streams affects production yield. If moisture concentrations exceed specified limits, the contaminated gas stream may produce, at considerable expense, an unacceptable semiconductor lot. Thus, detection and measurement of moisture concentrations in industrial processes such as semiconductor production is required because moisture is often critical to the quality of the product produced.

To meet the industrial demand, sensitive hygrometers are available which have extremely low detection limits and fast response times. The most sensitive and commercially available hygrometers can detect and measure moisture concentrations on the order of ten parts per billion by volume—although modern, high-purity hygrometers may reach limits of a few ppb. K. Sugiyama & T. Ohmi, "Ultraclean Gas Delivery Systems—Part I", in *Microcontamination* at 49-54 (Nov. 1988), discloses that gases with moisture levels on the order of two parts per billion can be produced and that such levels can be measured by Atmospheric Pressure Ionization Mass Spectrometry (APIMS). See also T. Kimura, J. Mettes & M. Schack, "Sub-ppb Analysis of Nitrogen Gas by APIMS", presented at the Technical Symposium of SEMICON EAST 89 in Boston, Mass. (Sept. 1989) (disclosing an experimental setup and a procedure for the analysis of high-purity nitrogen). The commercial devices usually include an alarm, which is activated once the moisture concentration of a sample gas stream exceeds a specified level.

Modern hygrometers also typically incorporate an electrolytic cell as the analytical component. The gas to be measured flows through the cell with a known flow rate. The moisture concentration of the gas is determined by absorbing the moisture from the gas, using an hygroscopic film, and electrolyzing the water absorbed in that film. Once equilibrium is achieved, the number of molecules electrolyzed per second, measured as the electrolysis current, is proportional to the number of water molecules entering the cell with the gas each second. An example of an electrolytic cell is described in U.S. Pat. No. 4,800,000 to D. A. Zatko, incorporated herein by reference.

Conventional hygrometers tend to react slowly to changes in moisture concentration when measuring very small concentrations. An unacceptable time lag of the hygrometer may occur, especially in response to a rise in moisture concentration, after the hygrometer is connected to a very dry gas for a long period. The presence of dry gas for a long time will cause the components of the hygrometer which contact the gas to become dry themselves. Those components include packing materials, like epoxy, which are known to be relatively porous and to absorb or emit moisture from or into a passing gas stream. Such components are described in a co-pending U.S. application Ser. No. 07/629,439 entitled "Counterflow Device and Method to Reduce the Negative Impact of Contaminating Materials Used in Moisture Sensitive Apparatuses or Procedures" and filed on Dec. 18, 1990 by Jacob Mettes. That application is incorporated herein in its entirety.

When an hygrometer encounters a dry gas having a moisture concentration below its detection limit, the instrument will produce a background level reading. In contrast to that reading and in reality, however, the hygrometer and its components will attain an equilibrium corresponding to the lower (undetectable) moisture level. When the moisture concentration subsequently changes to a higher level, certain internal components of the hygrometer will, because they are dry, absorb the moisture before the gas reaches the analyzer. Consequently, it will be some time before the hygrometer senses the increased moisture and can activate an alarm or show the higher concentration.

The amount of time depends, among other things, on how dry the gas was and on how long the dry gas flowed. The process monitored by the hygrometer may be using gas with an unacceptably high moisture concentration for a relatively long time, therefore, before the hygrometer "reads" the correct concentration and activates an alarm. For many applications, such a time lag is unacceptable.

In addition to the time lag discussed above, conventional hygrometers fail to address another matter: they do not provide automatic verification that the system is functioning. Many users of hygrometers would like verification that their instrument remains responsive to moisture. Users now verify responsiveness on occasion by introducing air and, therefore, moisture into the hygrometer and monitoring the hygrometer's response.

Although verification is achieved by that approach, there is little quantitative control on the amount of moisture introduced. The amount is, in fact, usually large. Consequently, the hygrometer components which absorb moisture will become wet at moisture concentrations typically far above the alarm levels. In such a case, the absorbed moisture will desorb slowly back into the gas flow once resumed and it will be some time before the hygrometer will effectively read the low moisture concentrations in the gas. Moreover, the approach is typically not automatic; the user must consciously decide to test the hygrometer.

SUMMARY OF THE INVENTION

Accordingly, one object of the present invention is to generate a gas stream with a controllable low concentration of moisture. Another object is to provide a method and an apparatus for reducing the response time required for an hygrometer to detect and measure an increase in the moisture concentration of the sample gas measured by the hygrometer. Another object of the present invention is to provide automatic verification that the hygrometer is responding to moisture.

To achieve these and other objects, and in view of its purposes, the present invention provides an apparatus which will add, and describes a method which includes adding, small amounts of moisture to the gas stream before it reaches the analyzer. The addition can be controlled by feedback from the hygrometer or can be made periodically. Such regular moisture additions enable the hygrometer itself to check its response automatically. They also prevent the hygrometer components from drying to levels far below the hygrometer's detection limit, thus assuring a fast response to an increase of moisture concentration in the sample gas.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

Figure 1:
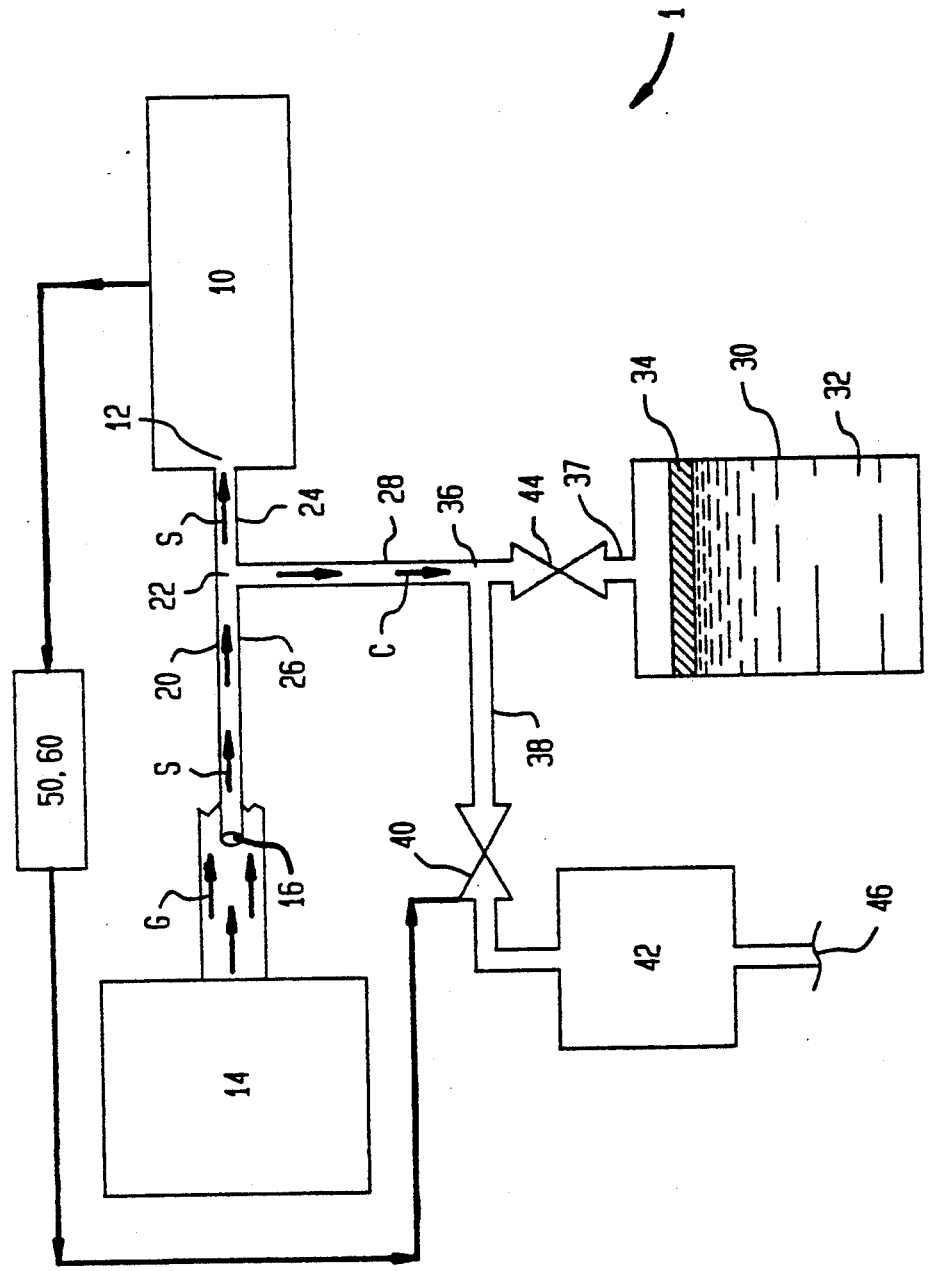
FIG. 1 illustrates the major components of an apparatus constructed in accordance with the present invention.

FIG. 1 shows an hygrometer-controlled moisture generator apparatus 1 which includes a conventional hygrometer 10 as described above. Hygrometer 10 provides a feedback signal and is tested "on line" to assure its proper and optimal functioning. Hygrometer 10 includes an inlet 12 for the sample gas flow, illustrated by the arrows designated "S".

Generally, hygrometer 10 will also include components which control and eventually measure the flow rate of the gas passing through it, a rate which is typically set at a fixed, stable value. If hygrometer 10 does not include such components, they may be provided externally and, for example, downstream from the hygrometer outlet. Such components would then comprise part of the apparatus necessary to operate the present invention. Even when the gas flow toward hygrometer 10 varies, however, which causes the change in the moisture concentration following the addition of moisture by the moisture generator apparatus 1 to vary, the feedback signal from hygrometer 10 will allow it to function properly. The feedback signal is activated when hygrometer 10 reaches certain moisture concentration levels regardless of instabilities, caused by unstable gas flow, in the rising readings toward those levels.

A tubing connector 20 connects the source 14 of the gas with inlet 12 of hygrometer 10. Between source 14 and inlet 12 there is provided a sampling point 16 where tubing connector 20 removes sample gas S from the larger gas stream, designated by arrows "G". Typically, tubing connector 20 is devoid of tributaries and is ¼-inch or ⅛-inch diameter, electropolished stainless steel.

For the apparatus of the present invention, however, tubing connector 20 is provided with a first "T" connection 22. Also of ⅛-inch or ¼-inch diameter, electropolished stainless steel, T connection 22 permits apparatus 1 to add moisture to sample gas S before gas S reaches hygrometer 10. To minimize travel of that moisture, T connection 22 is placed as close as practical to, and preferably within one or two inches of, inlet 12 of hygrometer 10. Thus, the length of right arm 24 of T connection 22 is as short as possible. The distance from T connection 22 to sampling point 16, which defines the left arm 26 of T connection 22, is also as short as possible. The short lengths allow the analyzer of hygrometer 10 to have a short response time upon changes in the moisture concentration of the gas stream.

The tubing leg 28 of T connection 22 extends toward and connects to a permeation device 30. Device 30 contains a source of moisture 32 for addition to hygrometer 10 and a membrane 34. To enter sample gas S at connection 22, moisture 32 must diffuse through membrane 34 and travel along tubing leg 28 until it reaches sample gas S at T connection 22.

As shown in FIG. 1, tubing leg 28 itself is part of a second "T" connection 36 (also of ⅛-inch or ¼-inch diameter, electropolished stainless steel). Tubing leg 28 of T connection 22 forms the left arm and the right arm of T connection 36. The portion of tubing leg 28 between T connection 36 and permeation device 30 is specifically designated the right arm 37 of T connection 36. The tubing leg 38 of T connection 36 engages a first valve 40 then, in turn, a flow control (FC) component 42. FC component 42 assures a constant flow through leg 38 when first valve 40 is open. FC component 42 can be purely mechanical, such as a combination of a needle valve and a pressure regulator or backpressure regulator. A mass flow controller, in which a flow rate sensor provides feedback to an electrically adjustable valve, is also suitable.

The distance from T connector 22 to T connector 36 must be sufficiently short to assure rapid migration when adding moisture, yet sufficiently long to permit the counterflow to prevent moisture addition, thus providing two modes of operation, namely, moisture addition on and moisture addition off. A distance of about two inches is suitable; such a distance ensures a sufficient counterflow even at low flow rates through leg 38. The physics and a numeric example showing the effectiveness of a "counterflow", as used to isolate sources of moisture, are described in the co-pending United States application entitled "Counterflow Device and Method to Reduce the Negative Impact of Contaminating Materials Used in Moisture Sensitive Apparatuses or Procedures" and mentioned above.

First valve 40 is an "on-off" type valve, as distinguished from a "needle" valve. Valve 40 is pneumatically or electrically switched. A second "on-off" valve 44 may be positioned, as an option, in right arm 37 of T connection 36. Second valve 44 is normally fixed permanently in the open position and is inactive; it is not essential to the operation of apparatus 1. Instead, second valve 44 is an optional convenience. The functions of valves 40 and 44 will become apparent in the description of the method of using the apparatus 1 described below.

In operation, a gas G to be monitored flows from its source 14. A portion of gas G enters tubing connector 20 at sampling point 16, Which corresponds to the end of left arm 26 of first T connection 22. That portion forms sample gas S and continues toward hygrometer 10, passing T connection 22 on its way.

If first valve 40 is open, an amount of sample gas S will be diverted at T connection 22 before reaching hygrometer 10. The diverted gas, Which flows into leg 28, is designated by the arrows labelled "C" in FIG. 1. (Because hygrometer 10 measures concentration, and not volume, the diversion of a small amount of sample gas S as counterflow gas C will not affect the analytical result of hygrometer 10 on sample gas S.) Gas C travels from T connection 22 toward permeation device 30 and, by forming a counterflow, prevents moisture 32 in device 30 from reaching sample gas S. Instead, gas 0 carries moisture 32 away from sample gas S, through FC component 42, and out exit 46 of apparatus 1.

The counterflow provided by gas flow C has proven very efficient. For example, a counterflow C of 100 cc/minute so effectively shields sample gas S from 1600 ng/minute of moisture 32 generated by permeation device 30 that sample gas S is contaminated by no more than 2 ppb of added moisture. Thus, even very small counterflows C are effective. The precise amount of counterflow C can be set by FC component 42.

If first valve 40 is now closed, counterflow C will stop and moisture 32 from permeation device 30 will begin to diffuse into that part of tubing leg 28 between T connection 36 and T connection 22—being initially absorbed by the walls of tubing leg 28 as it travels—until moisture 32 reaches and permeates into sample gas S at T connection 22. After a certain response time, hygrometer 10 will then start to detect and measure the increased moisture concentration of sample gas S. Hygrometer 10 will ultimately attain an equilibrium value representing the moisture concentration of sample gas S before it enters first T connection 22, as increased by the addition of moisture 32 from permeation device 30. That increased value will be determined by the permeation rate of moisture 32 from permeation device 30 and the flow rate of sample gas S into hygrometer 10.

As soon as first valve 40 is opened again, counterflow C will resume, thus preventing moisture 32 from reaching sample gas 8. The equilibrium moisture concentration value will then decrease and return to the level corresponding with the original moisture concentration in sample gas S. The response of hygrometer 10 will follow unless the moisture concentration falls below the detection limit of hygrometer 10, in which case the response of hygrometer 10 will indicate that limit.

In using apparatus 1, a systematic and automatic feedback loop 50 can be established to add finely controlled amounts of moisture 32 to sample gas S by opening and closing first valve 40 in response to the signal provided by hygrometer 10. An example of such a process is illustrated, in FIG. 2, for an hygrometer 10 with a detection limit of about 3 ppb (line "a" in FIG. 2) analyzing a very dry sample gas S containing a moisture concentration of about 3–4 ppb.

Three alarm levels are used in the example, two of which establish a band for the addition of moisture. The lower limit alarm for the band is set at 10 ppb (line "c" in FIG. 2); the upper limit alarm for the band is set at 15 ppb (line "d" in FIG. 2). When the signal of hygrometer 10 is below the lower limit alarm, first valve 40 is closed and the moisture addition is activated. Only when the signal of hygrometer 10 rises above the upper limit alarm will first valve 40 be reopened, stopping the moisture addition. After the moisture addition has been stopped, because hygrometer 10 attained a reading above the upper limit alarm, it will resume only when hygrometer 10 again attains a reading below the lower limit alarm.

Upon start-up of apparatus 1, moisture is added because hygrometer 10 reads a gas moisture concentration which is less than 10 ppb. The addition continues until hygrometer 10 reads a concentration at or above 15 ppb, whereupon the moisture addition stops. Thereafter, in the example of FIG. 2, first valve 40 remains open, creating a counterflow which prevents moisture addition (this is the mechanism used to stop the moisture addition), until hygrometer 10 again detects a moisture concentration below 10 ppb. When that occurs, first valve 40 is again closed (allowing moisture addition) until hygrometer 10 detects a moisture concentration at or above 15 ppb. The cycle described above may continue indefinitely.

Figure 2:
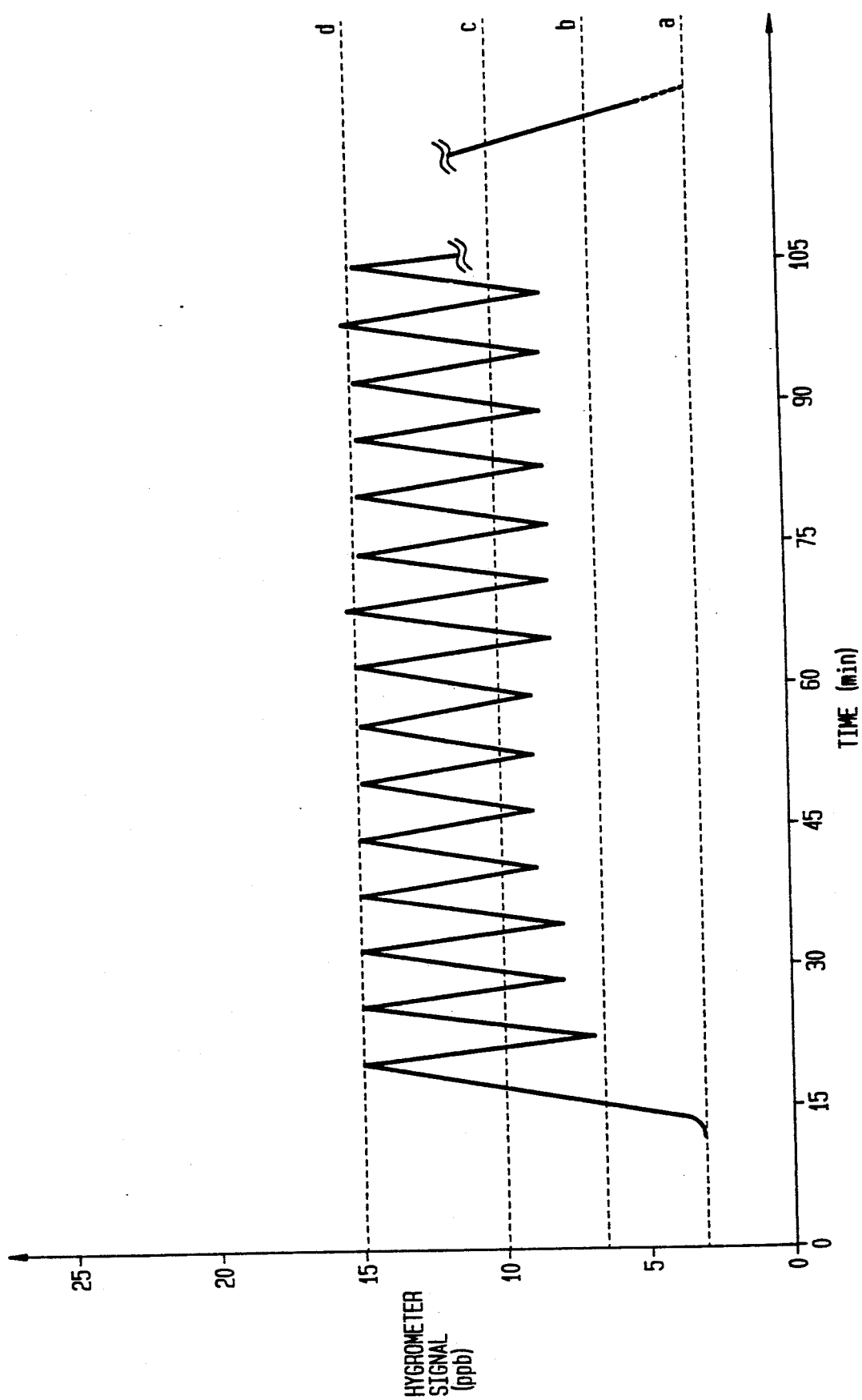
FIG. 2 is a graph showing an example response of the apparatus illustrated in FIG. 1 when operating in accordance with a first embodiment of the method of the present invention.

A useful observation of the performance of the apparatus used to produce the graph of FIG. 2 provides insight into the amount of moisture which is added. When moisture 32 generated by permeation device 30 was continuously added to the sample gas S in the example shown in FIG. 2, by maintaining valve 40 in the closed position, an equilibrium concentration of about 300 ppb was ultimately measured.

Feedback loop 50 (see FIG. 1) offers an automatic and frequent response check on hygrometer 10. As long as hygrometer 10 is functioning properly, it will respond to the small additions of moisture 32 in the pattern shown on the graph of FIG. 2. That response is indicative of the speed, stability, and proper functioning of hygrometer 10. The response of hygrometer 10 to both wetting and drying processes can be monitored separately by observing the rising and falling slopes, respectively, on the graph. Once set up, apparatus 1 will display such a pattern automatically, without user intervention.

The addition of moisture 32 to sample gas S will also maintain the average equilibrium value of hygrometer 10, ideally, just above the detection limit of the hygrometer. In the example of FIG. 2, the equilibrium value is maintained between 10–15 ppb for an hygrometer with a detection limit of about 3 ppb. Such additions assure that the instrument will be alert and will detect a moisture intrusion rapidly. Rather than first wetting the interior parts of the analyzer, typically necessary when those parts have become drier than the level of the detection limit, moisture intrusions can be detected more quickly because the starting moisture level is already at a higher level (10–15 ppb in the example of FIG. 2). Little information is lost by adding moisture in this way because, once the moisture concentration is at or below the detection limit, no additional information would be available anyway.

FIG. 2 also indicates a third alarm which is set between the detection limit of the hygrometer and the lower alarm limit (line c) of the moisture addition band. The additional alarm is represented by line "b" and has a set point of about 6-7 ppb for the example shown in FIG. 2. The alarm is activated when the moisture concentration, as read by the hygrometer, falls below the set point of that alarm—as shown by the right-most dip on the graph of FIG. 2. Thus, the additional alarm provides a convenient and reassuring feature for an hygrometer which is used to safeguard a gas stream in a moisture-critical application.

Once moisture additions are provided, the moisture level read by the hygrometer should never fall below the lower alarm limit of the moisture addition band; therefore, the additional alarm normally never activates. The additional alarm will be activated only when, despite sufficiently large moisture additions, the hygrometer fails to function properly. Activation means either that the hygrometer is not properly detecting moisture or that the moisture additions are not properly provided. It is reassuring for the user of an hygrometer which safeguards a gas stream in a moisture-critical application to know that a warning will be provided if the hygrometer becomes inactive.

Note that a typical alarm setting useful to warn against moisture intrusion in the sample gas, for the example of FIG. 2, might be about 100 ppb. When apparatus 1 engages a sample gas S containing, at a certain moment, a moisture concentration which is rising toward a level of 100 ppb or more, valve 40 will already be open (creating a counterflow which prevents moisture addition)—having opened as soon as hygrometer 10 reached a reading of 15 ppb. Thus, by the time the reading of hygrometer 10 reaches the alarm level of 100 ppb, no moisture will have been added to the gas stream for some time. That time is normally sufficient so that the impact of the last moisture addition on the accuracy of the alarm reading of hygrometer 10 will be negligible.

Moreover, experimental data obtained using the counterflow apparatus shown in FIG. 1 exhibit an almost instantaneous halt in the rising hygrometer signal monitoring a moisture addition upon activation of the counterflow. See the graph for the example shown in FIG. 2, which indicates that the rising hygrometer signal almost invariably stops precisely at 15 ppb—the point at which the counterflow is activated. That result is in contrast to the hygrometer reaction on wetting where the downward slopes in FIG. 2 continue beyond the level (10 ppb) where the counterflow stops. Such a contrast is explainable: the first moisture entering the dry components (e.g., tubing) of apparatus 1 upon the addition of moisture at 10 ppb is absorbed by those components and does not reach the analyzer of hygrometer 10. The moisture concentration falls about 2-3 ppb below the lower alarm limit of 10 ppb before the added moisture wets the components and reaches hygrometer 10. Such an effect should be taken into account, of course, when setting the additional alarm between the lower limit of the band and the detection limit of the hygrometer to avoid "false" alarms.

As the above description of the method of using the apparatus 1 makes clear, second valve 44 is not essential to operation of apparatus 1. Second valve 44 may be positioned in right arm 37 of T connection 36, however, for convenience. By closing valve 44, the user can remove permeation device 30 from the system if desired without perturbation. Such removal might be useful during transportation of apparatus 1. It is also helpful during hook up or shut down of apparatus 1.

Figure 3A:
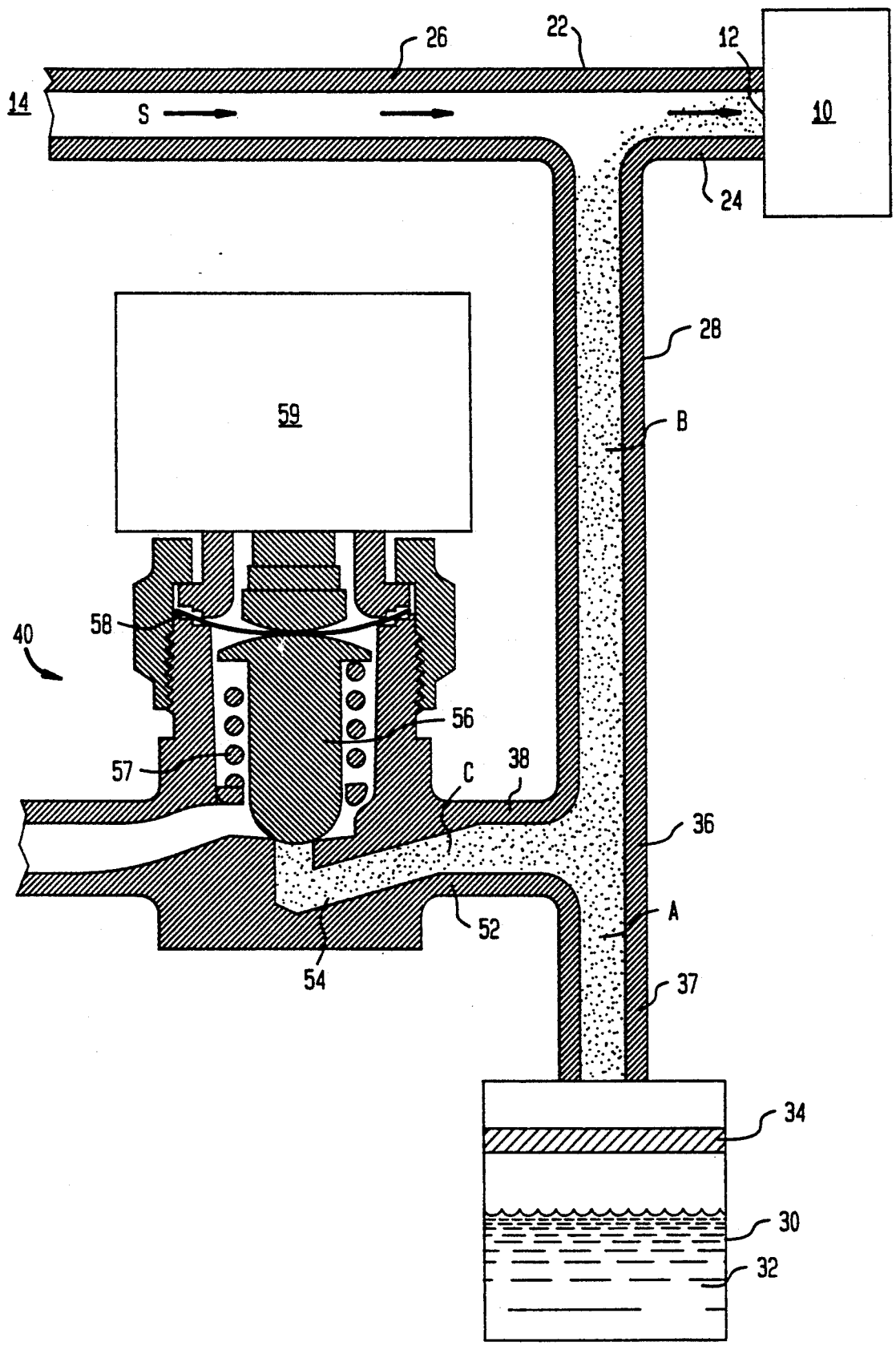
FIG. 3a shows the gas flow directions and the presence of moisture in the major components when the first valve of the apparatus shown in FIG. 1 is closed and moisture is added to the gas stream.
Figure 3B:
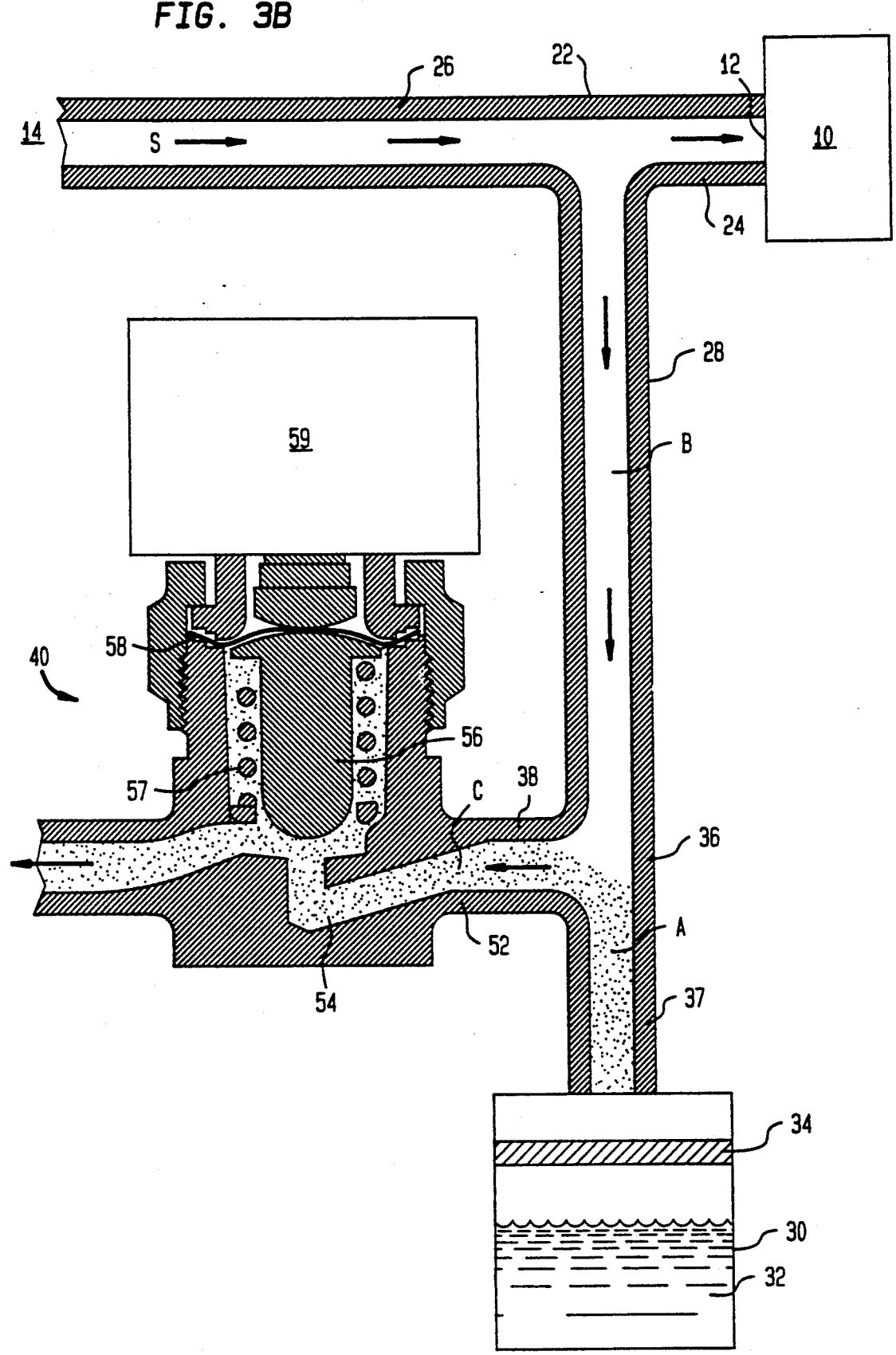
FIG. 3b shows the gas flow directions and the presence of moisture in the major components when the first valve of the apparatus shown in FIG. 1 is open and moisture is no longer added to the gas stream.

The counterflow mechanism will now be discussed in greater detail with reference to FIGS. 3a and 3b. FIG. 3a shows the flow of moisture when the first valve 40 of apparatus 1 is closed and moisture 32 from permeation device 30 is added to the sample gas S; FIG. 3b shows the flow of moisture when first valve 40 is open and moisture 32 is no longer added to sample gas S. The sample gas S shown in both figures is dry. Moisture is indicated with dots in FIGS. 3a and 3b and the behavior of that moisture in the various areas of the apparatus is discussed below for the two modes of operation, namely, where valve 40 is open or closed.

Area A: Inside right arm 37 of T connection 36 in FIGS. 3a and 3b moisture behaves essentially the same, with respect to the component (i.e., tubing wall) absorption/desorption moisture equilibrium, when valve 40 is closed (FIG. 3a) or open (FIG. 3b). In both cases, the same amount of water molecules will diffuse through membrane 34 per second. In equilibrium, the diffusion rate through membrane 34 will be the travel rate through right arm 37.

Area B: An inside portion of leg 28 of T connection 22 will become dry when valve 40 is open and the counterflow prevents moisture from entering leg 28. In contrast, moisture will wet leg 28 when valve 40 is closed and, once equilibrium is achieved, moisture will flow through leg 28 at the same rate as moisture 32 diffuses through membrane 34.

Area C: The inside of leg 38 of T connection 36 will always be wet, whether valve 40 is open or closed, although the degree of saturation will differ depending upon the presence or absence of a counterflow through leg 38. When a counterflow is present, the concentration of moisture in leg 38 will be more diluted.

Because "dead volumes" (those areas through which gas does not flow) are difficult to purge, the moisture content of such volumes is likely to be unstable and to vary with time and temperature. Long durations of outgassing will cause large amounts of moisture to accumulate in such volumes. Moreover, the phenomena of outgassing and absorption/desorption have a temperature-dependent behavior. Another concern with dead volumes is that such volumes respond to changes in moisture concentration relatively slowly. It should be noted that active components, such as pressure regulators, valves, needle valves, flow controllers, and the like all have, to some extent, "dead volumes." For the reasons mentioned above, dead volumes must be avoided as much as possible in the critical parts of a well-controlled, highly repeatable system capable of working at very low moisture concentrations.

In apparatus 1 of FIG. 1, all components receive a continuous flow whether or not the system is adding moisture. There are no "temporary" dead volumes whose moisture content will later contaminate sample gas S. Although a temporary dead volume is formed at the input area of valve 40 when valve 40 is closed (see FIGS. 3a and 3b), the moisture accumulated there will not reach and contaminate sample gas S once valve 40 is opened. Rather, the accumulated moisture will be carried away from sample gas S through FC component 42 (see FIG. 1) once valve 40 is opened. The input area of valve 40 includes an entrance 52, a short channel 54 towards the stem tip 56 of valve 40, and the part of stem tip 56 which contacts the gas inside channel 54 (see FIGS. 3a and 3b). Note that valve 40 also includes a spring 57, a diaphragm 58, and a pneumatic control 59.

A second embodiment of the present invention uses a feedback loop 60 which operates in a more sophisticated way than the feedback loop 50 mentioned above in the first embodiment and described with reference to FIG. 2. The second embodiment will be discussed with reference to FIG. 4. Feedback loop 60 continues to provide the user with information on the actual changes in the level of the moisture concentration in the sample gas S to be monitored. Loop 60 also provides a frequent check, however, on the responsiveness of hygrometer 10 and assures that hygrometer 10 will have its maximum alertness.

When moisture concentration levels approaching the detection limit of hygrometer 10 (which might vary from hygrometer to hygrometer even for the same type of hygrometer) are analyzed, and the response of hygrometer 10 shows a certain degree of stability over a period of time after a downward slope, one of two events can be assumed to have occurred. Either hygrometer 10 is actually measuring a stable, low level of moisture concentration in the gas or hygrometer 10 is "hanging" at its detection limit. Absent the moisture addition of the present invention, the only information obtainable in such cases would be the low reading itself. It usually is very difficult to discriminate between "real" low moisture levels in a dry gas or an hygrometer which is "hanging" at its detection limit.

Once hygrometer 10 has reached a stable, low moisture concentration reading, however, the moisture addition of the present invention can be activated. That addition can then be stopped as soon as some small amount (a few ppb's) of moisture is measured above the previously attained low reading. Once the addition is stopped, the system should wait until a stable, low reading is again attained for some time, after a downward slope, before the system again adds the same small amount of moisture. On one hand, the information obtained from the response of hygrometer 10 to the moisture addition provides a more or less frequent check on the responsiveness of hygrometer 10. On the other hand, by staying close to the actual moisture concentration level present in the sample gas to be monitored (within the few ppb's mentioned), information about the sample gas quality is provided. Moreover, the values registered just before each moisture addition should correspond to the actual moisture level in the sample gas (or to the detection limit of hygrometer 10) so that the system provides regularly precise moisture concentration values.

Figure 4:
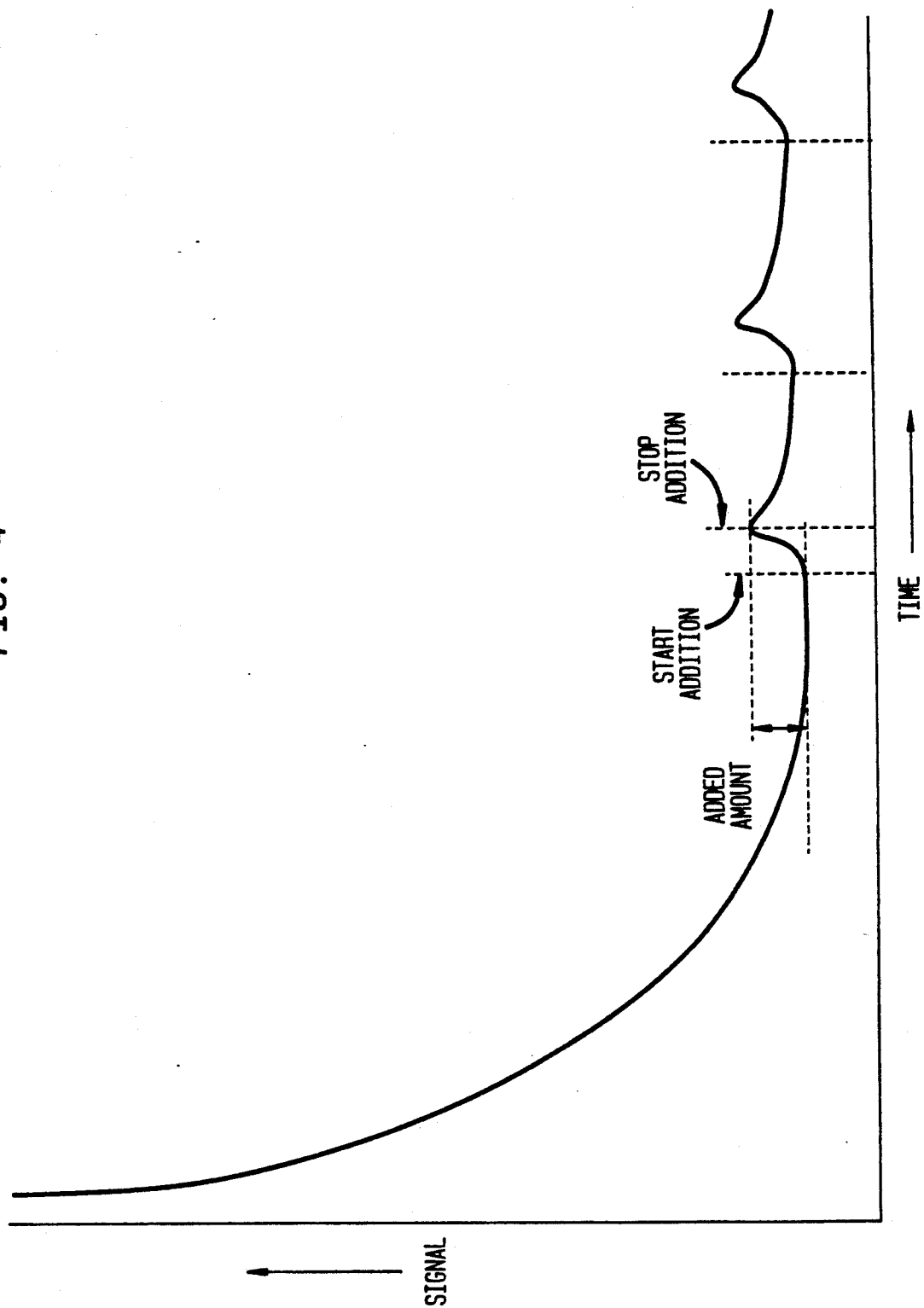
FIG. 4 is a graph showing an example response of the apparatus illustrated in FIG. 1 when operating in accordance with a second embodiment of the method of the present invention.

The relatively sophisticated feedback loop 60 can be achieved by a computer control of the moisture additions: a computer-activated signal opens or closes valve 40. The control would be based on information obtained from the response read (by the computer) from hygrometer 10 and from input data provided by the user. Such input need only be made once upon startup and the data would include stability criteria, the amount of moisture to be added, and the like. FIG. 4 shows a pattern that can be obtained using the sophisticated feedback loop 60 of the second embodiment of the present invention.

Figure 5:
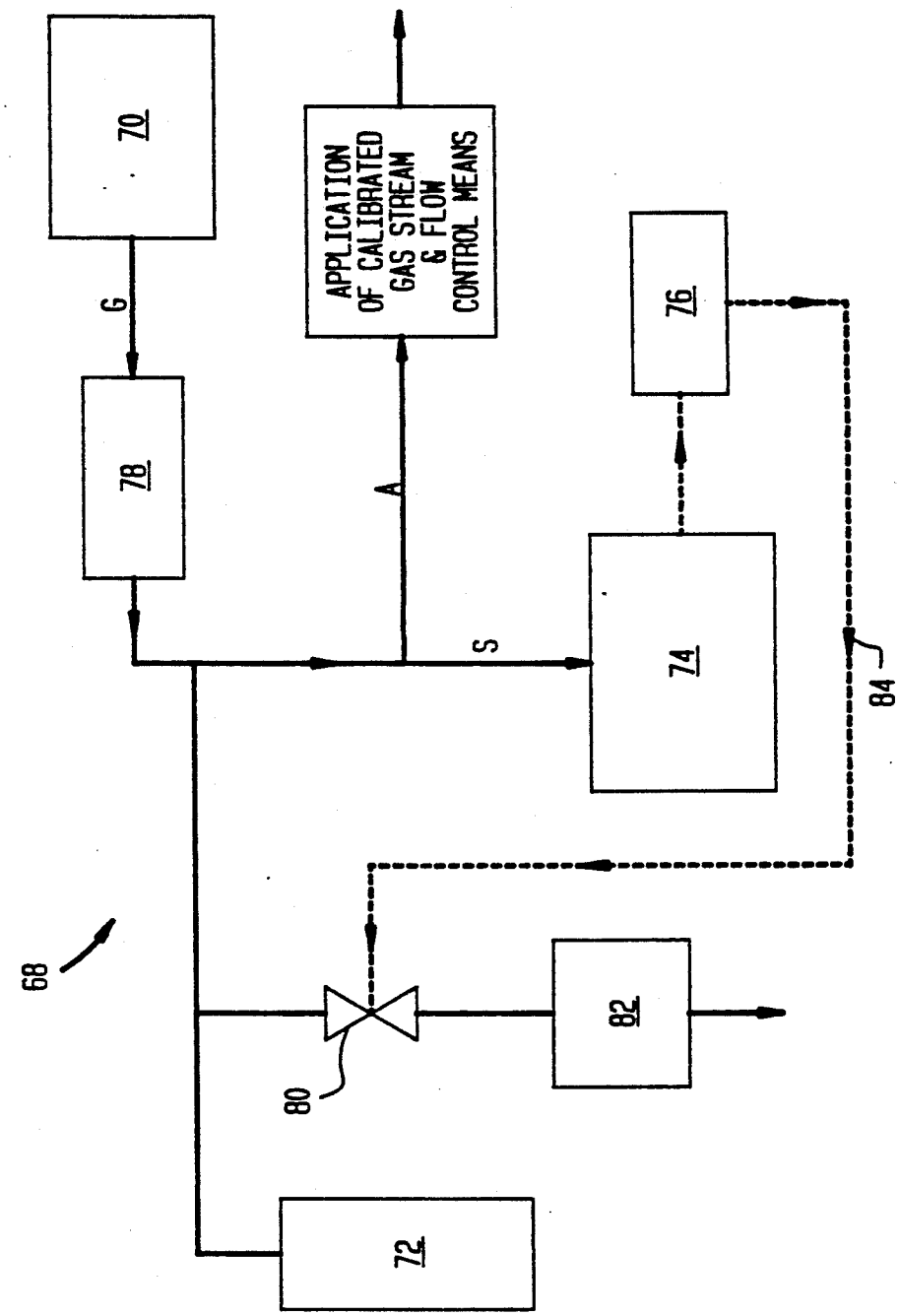
FIG. 5 shows a moisture generator according to the present invention.

FIG. 5 shows a moisture generator 68 according to the present invention. The main components and their functions are identical to those shown in FIG. 1. A gas source 70 provides a gas stream G. Gas stream G may have moisture added to it from permeation device 72—as regulated by valve 80 and FC component 82. Following possible moisture addition, gas stream G is split into two, separate gas streams: one stream forms sample gas S, which enters an analyzer 74, and another stream A becomes available for external use in the variety of applications for which moisture generator 68 is useful. Analyzer 74 provides feedback information to the feedback control 76. After incorporating that information, feedback control 76 sends a feedback signal 84 to open and close valve 80.

The input gas stream G of generator 68 may be purified in purifier 78. Thus, gas stream G may be purified (dry) gas or gas with an initial, and not necessarily stable, moisture concentration level. In this latter case, the lower limit of the operating range for the moisture generator 68 is restricted to the moisture concentration level already present in the input gas stream G.

Figure 6A:
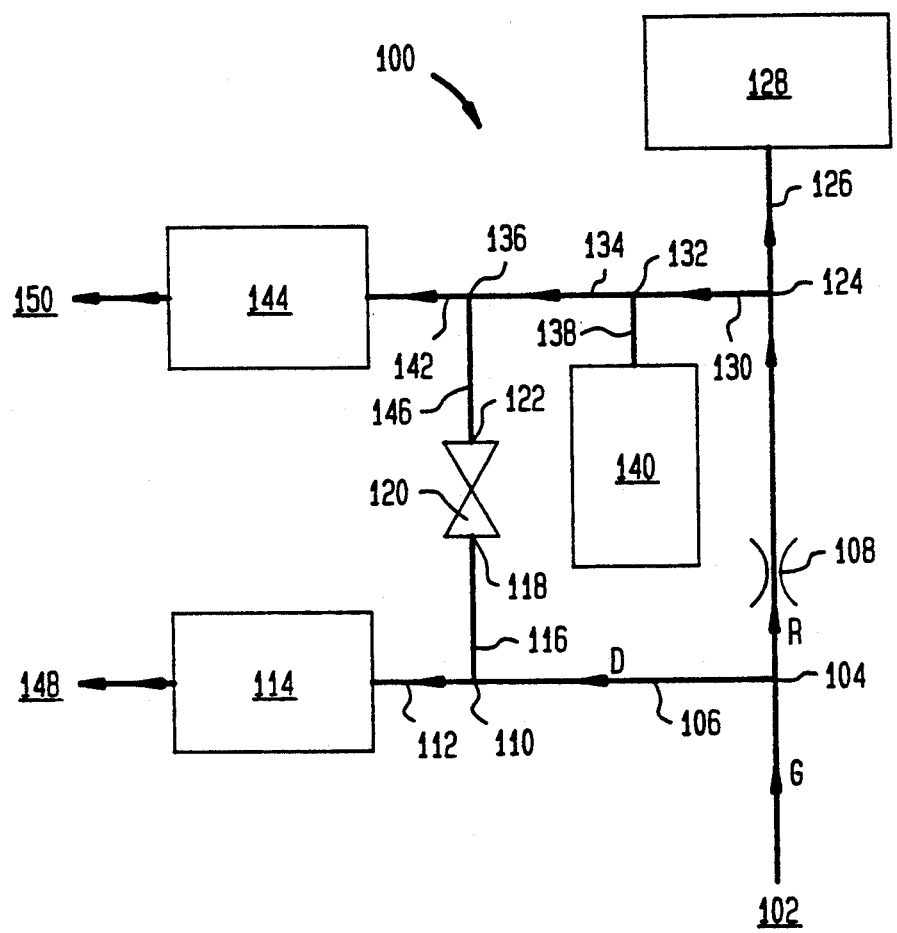
FIGS. 6a and 6b illustrate the major components of an apparatus constructed in accordance with, and which operates in accordance with a third embodiment of the method of, the present invention, in which a counterflow stops moisture addition to the sample gas and a gas flow is provided in the reverse direction when moisture is added.
Figure 6B:
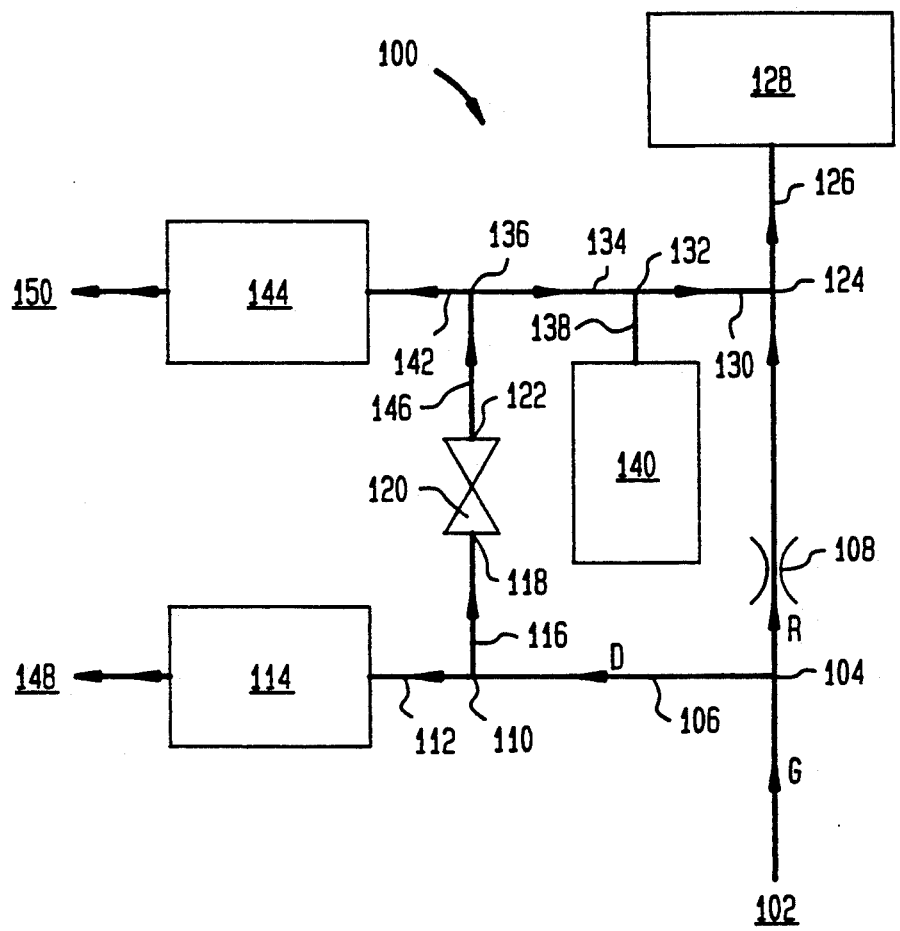

FIGS. 6a and 6b show a third embodiment of the present invention. Like the first two embodiments, that embodiment also uses a counterflow to stop moisture addition to the sample gas. The third embodiment uses a gas flow in the reversed direction, however, when adding moisture.

The incoming gas stream G enters apparatus 100 from gas source 102 and proceeds towards first "T" connection 104. At first T connection 104, a part of gas stream G is diverted into leg 106 of T connection 104 while the remainder R of gas stream G continues toward a flow restriction 108. The diverted gas D entering leg 106 flows towards a second "T" connection 110. At T connection 110, leg 106 splits again into leg 112, which engages a first FC component 114, and leg 116, which engages the input 118 of valve 120.

The remainder R of gas stream G which flows through restriction 108 will enter a third "T" connection 124. At third T connection 124, a split occurs into leg 126, which engages an analyzer 128, and leg 130, which engages a fourth "T" connection 132. T connection 132 splits again into a leg 134, which engages a fifth "T" connection 136, and a leg 138, which engages a permeation device 140. T connection 136 splits into a leg 142, which engages a second FC component 144, and a leg 146, which engages the output 122 of valve 120.

Gas flowing through FC component 114 and gas flowing through FC component 144 will exit apparatus 100 at outlets 148 and 150, respectively. Thus, these gases will be finally discarded and will no longer affect the operation of apparatus 100.

FIG. 6a shows apparatus 100 with valve 120 in the closed position, which means that moisture is not being added to the sample gas. When valve 120 is closed, diverted gas D Will flow away from the gas stream G. The amount of gas D which flows is determined by the first FC component 114 and ultimately by the gas pressure at the input of FC component 114. The flow of gas D will minimize the contaminating effect of the temporary dead volume including leg 116 and the closed input 118 of valve 120 because, in order to reach the gas stream G Which travels toward analyzer 128, contamination from that dead volume must travel against the (counter) flow through leg 106 formed by gas D.

A similar situation exists for leg 130, through which gas flows away from T connection 124. This gas creates a counterflow which prevents moisture from permeation device 140, and possible contamination moisture from the dead volume formed by leg 146, from entering the sample gas flowing toward analyzer 128. Instead, the moisture from permeation device 140 will enter the gas flow through leg 134 and Will ultimately pass through second FC component 144.

FIG. 6b shows apparatus 100 with valve 120 open, which means that moisture is being added to the sample gas. When valve 120 is open, the flow of diverted gas D will be larger through leg 106 than when valve 120 is closed. Although the size of the gas flow through first FC component 114 is unchanged, there is now an additional gas flow through valve 120. This additional gas flow passes through leg 146 after exiting valve 120 and will split at T connection 136. Part of that gas flow will pass into leg 142 and then into second FC component 144. The remainder Will flow into leg 134 towards analyzer 128. That remainder will receive moisture from permeation device 140 and will finally mix with a now much smaller gas flow R travelling through flow restriction 108. In fact, depending upon the size of flow restriction 108, a large part of the gas which enters analyzer 128 will have passed through valve 120.

Although the invention is illustrated and described herein as embodied in a small moisture addition apparatus which frequently and selectively, through use of a counterflow, adds a specified amount of moisture to a sample gas analyzed by an hygrometer to reduce the response time of the hygrometer and to provide automatic verification that the hygrometer is functioning, the invention is nevertheless not intended to be limited to the details shown. Rather, various modifications may be made in the details within the scope and range of equivalents of the claims and without departing from the spirit of the invention.

Specifically, the flow control (FC) component could be electrically activated and able to control within a certain range and continuously, rather than through an on-off mode, the flow rate of the counterflow gas removed through the component. The feedback signal could function to maintain the amount of the component, as detected by the analyzer, at a predetermined level by increasing the flow rate through the FC component when the amount of the component as detected is higher than the predetermined level and by decreasing the flow rate through the FC component when the amount of the component as detected is lower than the predetermined level.

The details of apparatus 1 illustrated in FIG. 1 may also modified by removing T connection 36, leg 38, first valve 40, and FC component 42. Instead of these components, valve 44 could be used to control the addition of moisture 32 (or another gas component) to sample gas S. Feedback signal 50, 60 would then control valve 44 rather than first valve 40.

An expedient choice of valve 44 would reduce the negative impact of the temporary dead volume created upon closure of that valve. An accumulation of moisture 32 (or another component) in the dead volume formed at the end of valve 44 facing permeation device 30 is unavoidable; such accumulation will cause irregularities in the addition of moisture 32. As discussed above, however, feedback signal 50, 60 will nevertheless maintain the readings of hygrometer 10 (or another analyzer) within the band illustrated, as an example, by FIG. 2. With respect to the opposite end of valve 44, the end shown connecting leg 28 in FIG. 1, the dead volume created at that end upon closing valve 44 (and thereby isolating permeation device 30) can be minimized by selecting a three-way valve as valve 44.

A three-way valve would integrate valve 44 directly with T connection 22. Such a valve typically has the same configuration as valve 40 shown in FIGS. 3a and 3b with one additional channel entering the cavity which contains spring 57. Illustrated channel 54, which can be closed by stem tip 56, would be connected to permeation device 30. The remaining two channels of the three-way valve would be connected to right arm 24 and left arm 26, respectively, of T connection 22. The volume of the three-way valve will thus be in the continuous and uninterrupted flow of sample gas S, thereby avoiding the effects of a "dead" volume.

Moreover, as discussed in the co-pending United States application entitled "Counterflow Device and Method to Reduce the Negative Impact of Contaminating Materials Used in Moisture Sensitive Apparatuses or Procedures" discussed above, a counterflow arrangement is helpful for detection devices which measure the content of components in a gas stream other than moisture. Such components might include, for example, oxygen, nitrogen, or carbon monoxide.

The apparatus and method of the present invention discussed above could easily be adapted to better detect and measure such components. A sensor able to detect and measure the specific component of interest would replace the hygrometer. The permeation device would contain that component instead of moisture, so that the apparatus could add small amounts of the component to the sample gas as needed.

What is claimed is:

1. A gas mixture generator comprising:
    a gas stream;
    a source of a component to be added to said gas stream;
    a connection from said source to said gas stream permitting the addition of said component to said gas stream;
    a leg positioned in said connection between said source and said gas stream through which gas from said gas stream can be removed;
    a counterflow formed in part of said connection when said gas is removed from said connection, said counterflow regulating the amount of said component added to said gas stream;
    means for controlling the amount of said gas from said gas stream which is removed through said leg;
    an analyzer able to detect said component in said gas stream and give information on the amount of said component present in said gas stream after said addition; and
    means for providing a feedback signal from said analyzer to said controlling means to control the amount of said gas from said gas stream which is removed through said leg.

2. A gas mixture generator as claimed in claim 1 wherein:
    said control means includes an electrically controllable mass flow control means adapted to control continuously the flow rate of said gas removed through said leg within a certain range, and
    said feedback means maintains the amount of said component as detected by said analyzer at a predetermined level by increasing the flow rate through said control means when said amount of said component as detected is higher than said predetermined level and by decreasing the flow rate through said control means when said amount of said component as detected is lower than said predetermined level.

3. A gas mixture generator as claimed in claim 1 wherein said feedback means includes:
an upper limit alarm set to activate when the concentration of said component as measured by said analyzer reaches a first predetermined level;
a lower limit alarm set to activate when the concentration of said component as measured by said analyzer reaches a second predetermined level which is lower than said first predetermined level; and
a band formed between said upper limit alarm and said lower limit alarm, whereby the amount of said component which is added to said gas stream is controlled to maintain the concentration of said component in said gas stream measured by said analyzer within said band.

4. A gas mixture generator as claimed in claim 3 further comprising a third alarm set to activate when the concentration of said component in said gas stream reaches a third predetermined level which is higher than said first predetermined level.

5. A gas mixture generator as claimed in claim 4 further comprising a fourth alarm set to activate when the concentration of said component in said gas stream reaches a fourth predetermined level which is lower than said second predetermined level, said fourth alarm warning when said gas mixture generator fails to function properly.

6. A gas mixture generator as claimed in claim 1 further comprising:
a purifier for purifying said gas stream of said component before said gas stream reaches said connection;
first and second legs which split said gas stream into a first and a second gas flow, respectively, after said gas stream has passed said connection, said first gas flow entering said analyzer; and
an outlet at the end of said second leg which makes said second gas flow available for applications of said gas mixture generator.

7. A gas mixture generator as claimed in claim 1 wherein said gas stream is a sample gas to be monitored by said analyzer and wherein said additions of said component to said gas stream are made to assure proper functioning of said analyzer.

8. A gas mixture generator as claimed in claim 7 wherein said feedback means includes a single manual interpretation of said information given by said analyzer after said analyzer has analyzed said sample gas for a time sufficient to produce meaningful information, said interpretation defining an appropriate cycle and duration time for adding said component to said sample gas, said cyclic additions assuring proper functioning of said analyzer.

9. A gas mixture generator as claimed in claim 8 wherein said cyclic additions of said component to said sample gas are sufficiently small to prevent perturbation of the analysis of said analyzer monitoring the concentration of said component in said sample gas.

10. A gas mixture generator as claimed in claim 7 wherein said feedback means automatically determines when said analyzer has reached a low component concentration level with sufficient stability using a predetermined criterion, generates a signal which starts adding said component to said sample gas upon making said determination, evaluates when said component concentration has increased a predetermined amount above said stable low component concentration level, and generates a signal which stops adding said component to said sample gas upon making said evaluation, whereby the response of said analyzer is automatically monitored.

11. A gas mixture generator as claimed in claim 10 wherein said additions of said component to said sample gas are sufficiently small to prevent perturbation of the analysis of said analyzer monitoring the concentration of said component in said sample gas.

12. A gas mixture generator as claimed in claim 1 wherein said source of said component is a permeation device including component and a membrane through which said component can diffuse.

13. A gas mixture generator as claimed in claim 12 wherein said component is moisture and said analyzer is an hygrometer.

14. A small moisture addition apparatus comprising:
a source of sample gas;
an hygrometer for detecting and measuring moisture in said sample gas, said hygrometer having a detection limit below which it cannot detect or measure moisture;
means connecting said hygrometer and said sample gas source for carrying said sample gas from said source to said hygrometer;
moisture addition means for selectively and automatically adding a specified amount of moisture to said sample gas to assure proper functioning of said hygrometer without perturbating said measuring of said hygrometer of said moisture in said sample gas beyond the accuracy of said hygrometer; and
means for limiting the amount of moisture added by said moisture addition means to an amount just above the detection limit of said hygrometer.

15. An apparatus as claimed in claim 14 wherein said adding means includes:
a permeation device including moisture and a membrane through which said moisture may diffuse;
a first leg connecting said permeation device to said connecting means for allowing said moisture of said permeation device to permeate said sample gas in said connecting means; and
means for selectively creating a counterflow in said first leg, said counterflow creating means adapted to prevent said moisture in said permeation device from permeating said sample gas in said connecting means when said counterflow creating means are in a first position and to allow said moisture in said permeation device to permeate said sample gas in said connecting means when said counterflow creating means are in a second position.

16. An apparatus as claimed in claim 15 wherein said counterflow creating means includes:
a valve having an open position allowing gas to flow through said valve and a closed position preventing gas from flowing through said valve, said open position corresponding to said first position of said counterflow creating means and said closed position corresponding to said second position of said counterflow creating means;
a second leg connecting said first leg to said valve; and
a flow control means positioned on the side of said valve opposite said second leg to assure steady gas flow when said valve is open.

17. A small moisture addition apparatus comprising:
a source of sample gas;
an hygrometer for detecting and measuring moisture in said sample gas;
means connecting said hygrometer and said sample gas source for carrying said sample gas from said source to said hygrometer;
a permeation device including moisture and a membrane through which said moisture may diffuse;
a first leg connecting said permeation device to said connecting means for allowing said moisture of said permeation device to permeate said sample gas in said connecting means;
a second leg connected on one of its ends to said first leg;
a valve connected to the other end of said second leg and having an open position allowing gas to flow through said valve and preventing said moisture in said permeation device from permeating said sample gas in said connecting means and a closed position preventing gas from flowing through said valve and allowing said moisture in said permeation device to permeate said sample gas in said connecting means, said valve selectively creating a counterflow in said first leg; and
a flow control means positioned on the side of said valve opposite said second leg to assure steady gas flow when said valve is open.

18. A small moisture addition apparatus as claimed in claim 17 further comprising an alarm which activates when the moisture concentration of said sample gas passes an undesirable amount.

19. A small moisture addition apparatus as claimed in claim 17 further comprising a second valve positioned in said first leg between said second leg and said permeation device, said second valve removing said permeation device as an active component from said apparatus when said second valve is in its closed position.

20. A small moisture addition apparatus as claimed in claim 17 wherein:
said connecting means and said first leg join to form a first "T" connection and said first leg and said second leg join to form a second "T" connection;
said hygrometer has an inlet;
the length of said connecting means between said inlet of said hygrometer and said first "T" connection is between about one to two inches; and
the length of said first leg between said first "T" connection and said second "T" connection is about two inches.

21. A small moisture addition apparatus as claimed in claim 17 wherein said connecting means, said first leg, and said second leg are electropolished stainless steel tubing with a diameter between ¼ and ½ inches.

22. An apparatus, for detecting and measuring a component in a sample gas, comprising:
a source of sample gas;
a sensor for detecting and measuring said component in said sample gas;
means connecting said sensor and said sample gas source for carrying said sample gas from said source to said sensor; and
means for selectively adding a specified amount of said component to said sample gas, said adding means including:

(a) a permeation device containing said component sought to be detected and measured by said sensor,
(b) a first leg connecting said permeation device to said connecting means for allowing said component of said permeation device to permeate said sample gas in said connecting means, and
(c) means for selectively creating a counterflow in said first leg between said permeation device and said connecting means, said counterflow creating means adapted to prevent said component in said permeation device from permeating into said sample gas entering said sensor when said counterflow creating means is in a first position and to allow said component in said permeation device to permeate into said sample gas entering said sensor when said counterflow creating means is in a second position.

23. An apparatus as claimed in claim 22 wherein said counterflow creating means includes:
a valve having an open position allowing gas to flow through said valve and a closed position preventing gas from flowing through said valve, said open position corresponding to said first position of said counterflow creating means and said closed position corresponding to said second position of said counterflow creating means;
a second leg connecting said first leg to said valve; and
flow control means positioned on the side of said valve opposite said second leg to assure steady gas flow when said valve is open.

24. A method for analyzing the amount of moisture in a sample gas which comprises the steps of:
(a) providing an apparatus of claim 16 having an hygrometer with a specified moisture concentration lower detection limit; and
(b) controlling the valve of said apparatus to maintain the moisture concentration of said sample gas between a lower equilibrium concentration which is slightly above said lower detection limit of said hygrometer and an upper equilibrium concentration which is a few ppb higher than said lower equilibrium concentration when the moisture concentration of said sample gas is below said upper equilibrium concentration;
(c) determining the moisture concentration of the sample gas to be analyzed by said hygrometer of said apparatus;
(d) adding moisture to said initial sample gas if said sample gas has a moisture concentration of less than said first equilibrium concentration until said sample gas has a concentration equal to said second equilibrium concentration; and
(e) monitoring the moisture concentration reading of said hygrometer.

25. A process as claimed in claim 24 wherein said step (b) of controlling said valve of said apparatus includes setting said valve to close when said moisture concentration of said sample gas is equal to said first equilibrium concentration and to open when said moisture concentration of said sample gas is equal to said second equilibrium concentration.

26. A process as claimed in claim 25 wherein said step (e) of monitoring said reading of said hygrometer is performed by a computer.

* * * * *